United States Patent [19]

LeFebre et al.

[11] Patent Number: 4,786,171
[45] Date of Patent: Nov. 22, 1988

[54] SPECTRAL ANALYSIS APPARATUS AND METHOD

[75] Inventors: David A. LeFebre; Roger E. Schirmer, both of Folsom, Calif.

[73] Assignee: Guided Wave, Inc., El Dorado Hills, Calif.

[21] Appl. No.: 891,273

[22] Filed: Jul. 29, 1986

[51] Int. Cl.$^4$ .......................... G01J 3/42; G01N 21/05
[52] U.S. Cl. ....................... 356/326; 356/246; 356/413; 356/436; 356/440
[58] Field of Search ............. 356/300, 244, 246, 409, 356/413, 414, 433, 434, 436, 437, 36, 300, 319, 326, 328, 402, , 432, 440, 244, 246; 250/227

[56] References Cited

U.S. PATENT DOCUMENTS

| | | | |
|---|---|---|---|
| 2,684,609 | 7/1954 | Becker | 356/413 |
| 2,690,695 | 10/1954 | Coates | 356/246 |
| 3,141,094 | 7/1964 | Strickler | 356/440 |
| 3,740,156 | 6/1973 | Heigl et al. | 356/440 |
| 4,509,212 | 4/1985 | Baker | 250/227 |
| 4,519,710 | 5/1985 | Luce et al. | 356/413 |

FOREIGN PATENT DOCUMENTS

| | | | |
|---|---|---|---|
| 0145877 | 6/1985 | European Pat. Off. | 356/36 |
| 0159907 | 4/1983 | German Democratic Rep. | 356/436 |
| 0039431 | 4/1981 | Japan | 356/402 |

OTHER PUBLICATIONS

Levine et al., IBM Technical Disclosure Bulletin, vol. 18, No. 11, Apr. 1976, pp. 3754–3756.

Primary Examiner—F. L. Evans
Attorney, Agent, or Firm—Poms, Smith, Lande & Rose

[57] ABSTRACT

Apparatus and method for measuring the absorbance of fluid samples. The length of the light path through the sample is adjusted to optimize the amount of light absorbed by the sample, and the absorbance of the sample is calculated from the length of the path and the amount of light absorbed. Accurate measurement of the absorbance of the fluid may be made by taking measurements at two different path lengths, since light level changes due to fouling of the optical windows or other slow changes in the optical train are independent of the path length, while that of the fluid varies proportionally with the path length. A preferred form of probe includes a cylindrical cell having an exposed variable path length sensing portion at one end and an actuator for varying the spacing at the other end, and a cylindrical cell insertion tube having seals and a large valve mechanism to permit removal of the probe without loss or escape of the fluid being measured.

7 Claims, 2 Drawing Sheets

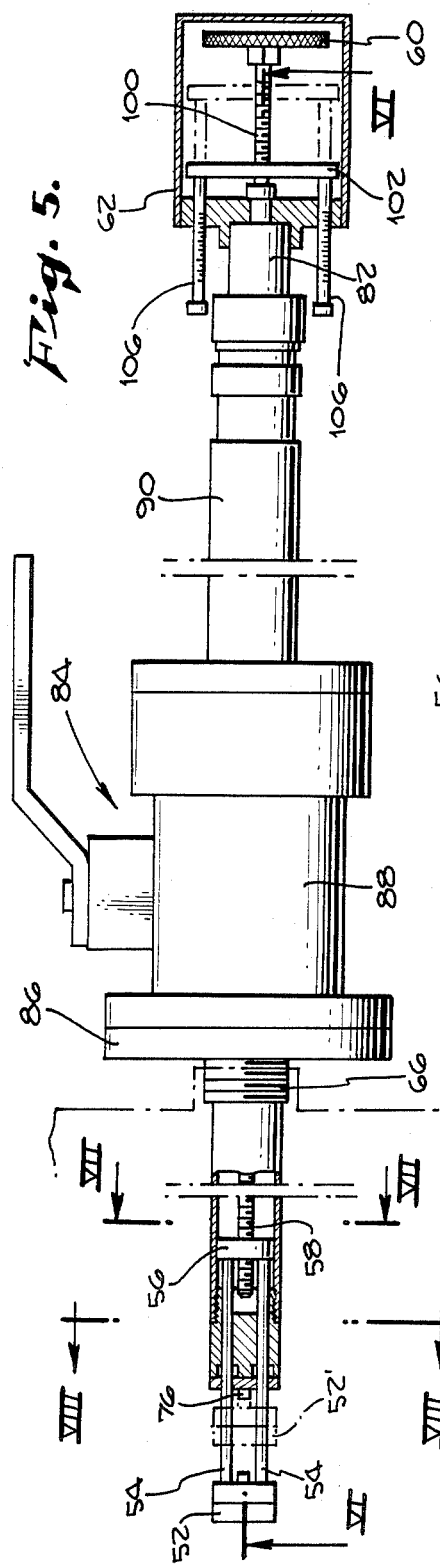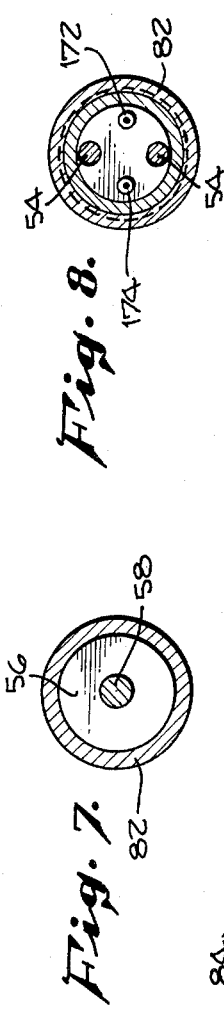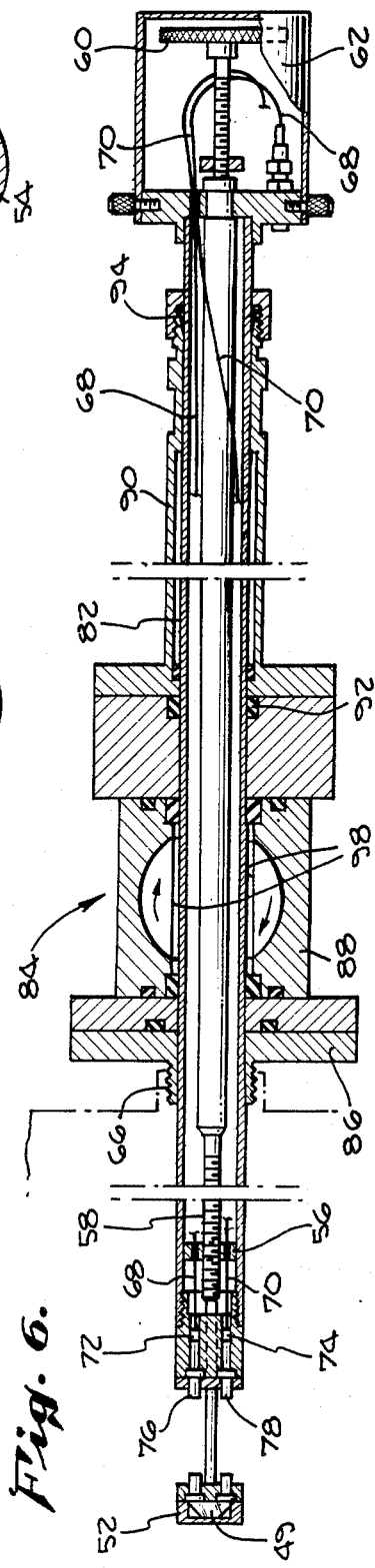

SPECTRAL ANALYSIS APPARATUS AND METHOD

FIELD OF THE INVENTION

This invention pertains generally to spectral analysis, and more particularly to apparatus and a method for making absorbance measurements over a wide range of absorptivities and concentrations.

BACKGROUND OF THE INVENTION

Liquid chemical absorbance measurements using conventional spectrometers employ cuvettes of fixed path length for holding the sample of the analyzed. If the concentration or absorbance of the sample is too high, the instrument may not measure the correct absorbance value due to limited polychromatic light scattering from the diffraction grating in the instrument. If the absorbance is too low, the resolving capability of the instrument may be exceeded due to noise limitations established by the detector, amplifiers and/or source or too low a light level measured by the detector. For each instrument there is an optimum range of absorbance values which have the best resolution, lowest noise and best linearity. However, with the concentrations of liquids available and the fixed path length of light passing through the liquid, the absorbance does not always fall within the optimum range for the instrument. In addition, if the path length of the cell is too short, it may be difficult to get the liquid sample into the cell. It is also possible to have within a given spectrum two or more absorbance peaks located in different portions of the spectrum which cannot both be accurately measured because the cell path length has been optimized for the absorbance typical of only one of them. A single path length can only quantitate optimally one absorbance peak if there is a large difference is absorbance values between peaks.

Another problem which may arise in the course of measurement of certain types of fluids is the formation of a coating on the window of the spectrophotometry cell. Such a coating may substantially reduce the light transmission through the cell, resulting in a change in signal level which is confounded with changes in sample absorption in conventional spectrophotometers.

It is in general an objective of the invention to provide a new and improved apparatus and method for making absorbance measurements.

Another objective of the invention is to provide an apparatus and method of the above character which overcome the limitations, problems and disadvantages of the absorbance measuring instruments as discussed hereinabove.

SUMMARY OF THE INVENTION

This and other objectives are achieved in accordance with the invention by varying the length of the path of light passing through the sample, to optimize the amount of light absorbed by the sample, and to calculate and differentiate between the fixed absorbance of a film on the windows and the variable absorbance with distance of the fluid being measured. The amount of light passing through the sample can be monitored, and the length of the path can be adjusted to maintain this light at a level which is optimum for the instrument which analyzes the sample. The path length can be modulated about this optimum length (or some other suitable length). The relationship between the amount of light absorbed and the length of the path is known, and the true absorbance of the sample can be calculated from the measured absorbances and the lengths of the paths. In addition, the path length may be decreased after the liquid is introduced into the cell, thereby insuring that the liquid will fill the light path regardless of how short the path may be.

In accordance with a more specific aspect of the present invention, a spectrophotometry system may include an elongated cell insertion tube having an integral enclosing housing, a variable length spectrophotometry cell having a cylindrical external surface making a close fit with the insertion tube, arrangements such as pipe threads for securing the insertion tube to a container or conduit containing the fluid to be measured, a valve mounted on said insertion tube adjacent the securing arrangements for selectively closing off the insertion tube; and a seal between the insertion tube and the outer surface of the cylindrical cell for permitting withdrawal of the cell beyond the valve, and closure of the valve to permit full removal of the cell without loss or escape of the fluid being tested.

Further, the variable length cell may include external spacing control and path length measurement arrangements operable to change the optical test spacing within the container or conduit when the cell unit is fully inserted. The cell may include a reflective prism spaced from the input and output optical waveguides, and with the prism being mounted on a pair of guide rods to maintain optical alignment as the prism is advanced and retracted.

From a method standpoint, it is desirable to initially calibrate the associated spectrophotometer relative to at least one known spectral frequency using monochromatic light routed through the entire optical system. In addition, an amplitude vs. frequency sample should be taken, preferably with at least two different spacings of the prism to provide different path lengths, with the sample cell being free of the fluid to be measured. Subsequently, using these background measurements, and amplitude vs. spectral frequency characteristics taken at two different spacings, the effect of possible filming of the sensor surfaces (constant with different spacing) may be separated from the response characteristic of the fluid sample (linear increase of absorbance with distance).

Other objects, features and advantages of the invention will become apparent from a consideration of the following detailed description and the accompanying drawings.

BRIEF DESCRIPTION OF THE DRAWINGS

FIG. 5 is a partial cross-sectional top view of a spectrophotometry cell illustrating the principles of the present invention;

FIG. 6 is a cross-sectional side view of the cell of FIG. 5; and

FIGS. 7 and 8 are cross-sectional views taken along lines VII—VII and VIII—VIII of FIG. 5.

DETAILED DESCRIPTION OF THE INVENTION

Figure 1:
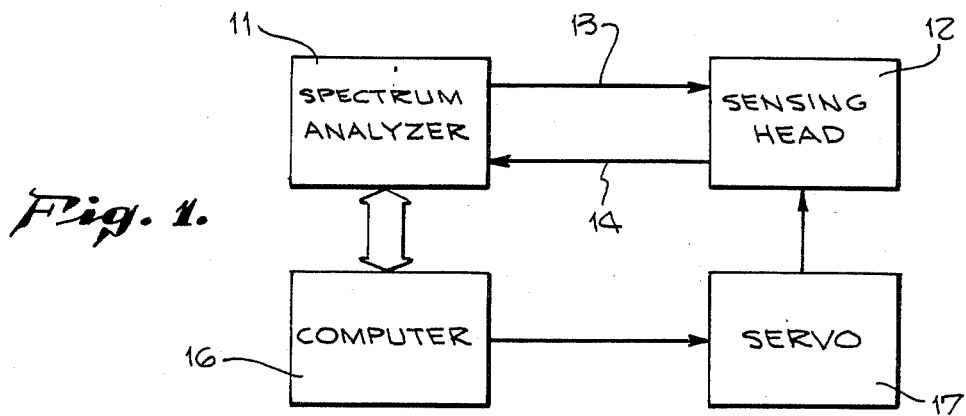
FIG. 1 is a block diagram of one embodiment of apparatus for measuring absorbance according to the invention.

As illustrated in FIG. 1, the apparatus comprises a spectrum analyzer 11 with a remote sensing head 12 connected to the analyzer by optical fiber waveguides 13, 14. The spectrum analyzer can be of the type disclosed in Ser. No. 644,325, filed Aug. 24, 1984, now U.S. Pat. No. 4,664,522, and is has a computer 16 associated with it. Waveguide 13 carries light from a source within the analyzer to the sensing head where it is passed through a sample (not shown), and waveguide 14 carries the light from the sample back to the analyzer. Each of the optical waveguides is preferably a single strand optical fiber for purity of optical transmission, and low cost, as compared with optical channels including bundles of optical fibers.

As discussed more fully hereinafter, sensing head 12 includes means for varying the length of the light path through the sample. A servo mechanism 17 controlled by computer 16 is connected to the sensing head to control the length of the light path.

Figure 2:
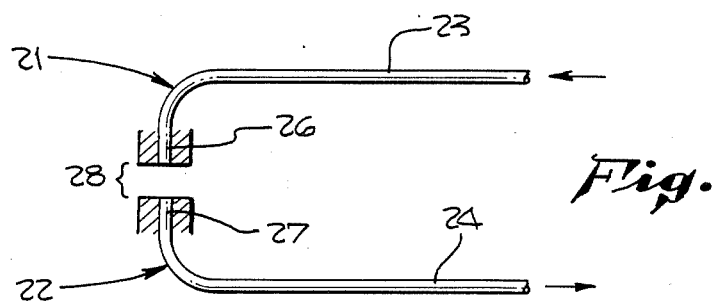
FIG. 2 is a cross-sectional view, somewhat schematic, of one embodiment of a sensing head for use in the apparatus of FIG. 1.

FIG. 2 illustrates one embodiment of a sensing head which can be utilized in the apparatus of FIG. 1. This sensing head comprises a pair of probes 21, 22 having optical fiber waveguides 23, 24 connected respectively to waveguides 13, 14. The confronting ends 26, 27 of waveguides 23, 24 are aligned axially on opposite sides of a gap 28 for transmitting and receiving light through the sample to be analyzed. The length of the path of light passing through the sample is determined by the width of gap 28, and the position of one or both of the probes is adjustable to vary the width of the gap. This sensing head is particularly suitable for use in applications where it is submerged in the liquid sample to be analyzed such as a vat or tank or in a stream of flowing liquid.

Figure 3:
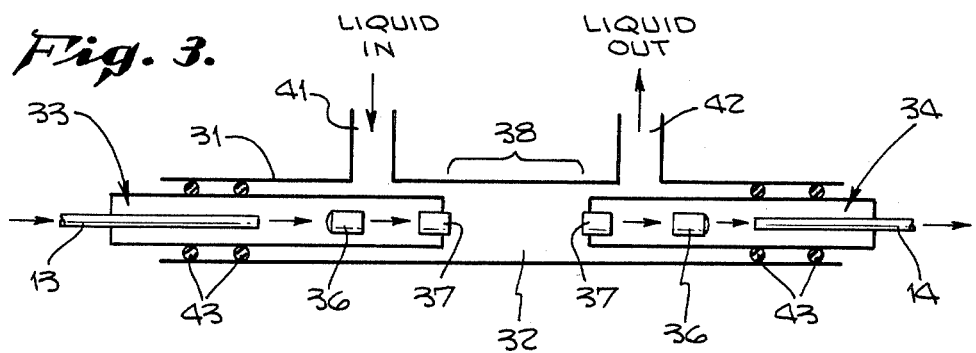
FIG. 3 is a cross-sectional view, somewhat schematic, of another embodiment of a sensing head for use in the apparatus of FIG. 1.

The sensing head of FIG. 3 includes a pipe 31 which defines a chamber or cell 32 which contains the sample to be analyzed. Probes 33, 34 are connected to waveguides 13, 14 and are aligned axially within the pipe on opposite sides of chamber 32. Each of the probes includes a cylindrical lens 36 which collimates the light, and a light transmissive window 37 at its inner end. The length of the light path 38 in the sample is determined by the distance between the probes, and one or both of the probes is movable to vary the length of the light path. The liquid sample flows into the chamber through an inlet 41 and flows through an outlet 42. Seal rings or rubber O-rings 43 close the ends of the chamber and provide fluid-tight seals between the outer walls of the probes and the inner wall of the pipe.

Figure 4:
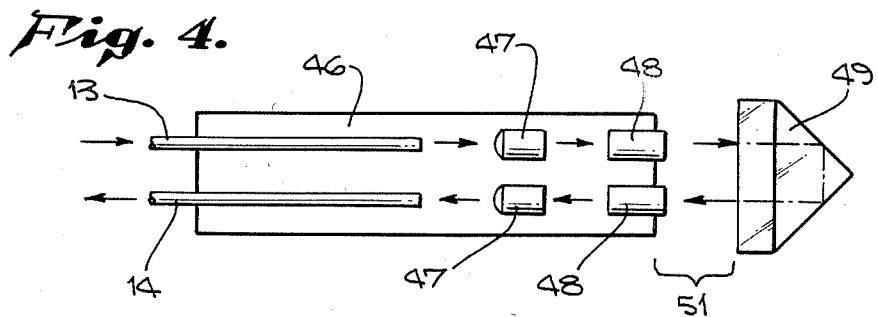
FIG. 4 is a cross-sectional view, somewhat schematic, of another embodiment of a sensing head for use in the apparatus of FIG. 1.

The sensing head of FIG. 4 includes a single probe 46 to which optical waveguides 13, 14 are connected. Collimating lenses 47 and windows 48 are aligned with the waveguides. A light reflector or prism 49 is spaced axially from the ends of windows 48. The reflector 49 receives light passing through the sample from waveguide 13 and directs this light back through the sample to waveguide 14. The separation 51 between the end of the probe and the reflector determines the length of the light path in the sample, and this distance can be adjusted by moving either the probe or the reflector, or both. The reflector can be of any suitable type, and in one presently preferred embodiment, it comprises a corner cube or prism.

In all of the sensing heads described herein, the movable probe or probes can be driven by any suitable mechanism such as mating screw threads, a rack and pinion gear, a cam and piston, a linear motor, a piezoelectric crystal or a hydraulic ram. The drive mechanism can be driven by any suitable means such as a stepper motor or a servo motor, and the positions of the movable elements can be monitored by suitable means such as an optical encoder, a conductive plastic linear or rotary potentiometer; or, for extremely critical path length determinations, an interferometer may be used. This sensing head configuration of FIG. 4 is particularly suitable for use in a fluid path where the entire sensing head is immersed in the fluid being measured.

Absorbance is given by the equation A=ebc, where "e" is the molar absorptivity of the sample in liter/c-mmole, "b" is the path length of the cell in centimeters, and "c" is the concentration of the absorbant material in moles/liter. From this relationship, it will be noted that absorbance is linearly proportional to the path length. A short path length would reduce the light loss through the sample for a highly absorbing fluid, while an extended path length would reduce the loss in absorbance resolution for dilute samples.

With a conventional single beam spectrometer, absorbance is commonly measured by first scanning a reference at every wavelength of interest, then scanning the specimen through the same spectrum. The absorbance for each wavelength, $\lambda$, is given by the relationship:

$$A(\lambda, L_o) = \text{Log} \frac{P_o(\lambda, L_o)}{P(\lambda, L_o)} \quad (1)$$

where $P_o(\lambda, L_o)$ is the reference light amplitude for path length $L_o$, and $P(\lambda, L_o)$ is the sample light amplitude for path length $L_o$.

When the length of the light path is varied, as in the present invention, the measured absorbance is given by the relationship:

$$A_m(\lambda, L) = \left[ \text{Log} \frac{P_o(\lambda, L_o)}{P(\lambda, L_o)} \right] \frac{L}{L_o} \quad (2)$$

where $L_o$ is the length of the path for the reference at wavelength $\lambda$, and L is the length of the path for the sample at wavelength $\lambda$.

As an example, consider a sample solution which displays an absorbance as follows with a light path length of 1 cm:

| Wavelength | Absorbance A (1 cm) |
|---|---|
| 200 nm | 20,000 |
| 225 nm | 12,000 |
| 250 nm | 5,000 |
| 275 nm | 1,000 |
| 300 nm | 500 |
| 325 nm | 250 |
| 350 nm | 50 |
| 375 nm | 1 |
| 400 nm | 0.3 |

In the foregoing table the wavelengths are given in nanometers (nm).

For a spectrum analyzer with a maximum linear dynamic range of 1.5 Au (Absorbance Units), it is desirable to use a path length which limits the absorbance of the sample to no more than 1.5 Au. If the reference is scanned at a path length $L_o$ and the sample is scanned at a path length L, then the measured absorbance $A_m$ can be determined from the reference absorbance A by the relationship:

$$A_m = A \frac{L}{L_o} \quad (3)$$

In the previous example, if the reference is taken at a path length of 1 cm in either air or a solvent that is low in absorbance (i.e. less than 0.5 Au) and the sample is taken at varying path lengths to limit the maximum difference in absorbance between the reference and the sample, to 1 Au or less at each wavelength, the relationship between the path length, measured absorbance and reference absorbance is as follows:

| Wavelength | Path Length | Measured Absorbance | Reference Absorbance A @ 1 cm |
|---|---|---|---|
| 200 nm | 0.5 μm | 1 | 20,000 |
| 225 nm | 0.833 μm | 1 | 12,000 |
| 250 nm | 2 μm | 1 | 5,000 |
| 275 nm | 10 μm | 1 | 1,000 |
| 300 nm | 20 μm | 1 | 500 |
| 325 nm | 40 μm | 1 | 250 |
| 350 nm | 200 μm | 1 | 50 |
| 375 nm | 1 cm | 1 | 1 |
| 400 nm | 1 cm | 0.3 | 0.3 |

In the foregoing table, the designation "μm" means micro-meters or $10^{-6}$ meters as compared with centimeters (cm) which are $10^{-2}$ meters.

In addition to keeping the absorbance measurements within the optimum range for a given instrument, the variable path length has a further advantage in that it makes it relatively easy to get the sample fluid into gaps or light paths of any length. With cells having fixed path lengths, it can be difficult to get a highly viscous fluid sample into a path of relatively short length. With the variable path length, the fluid can be introduced when the gap is relatively wide, and the gap can be closed to provide the desired path length with the fluid in position.

In the event that the light throughput of the cell is affected by the path length due to light losses not related to absorption by the sample, any resulting errors can be eliminated by either rerunning the reference after the sample is measured, using the same path lengths that were established for the sample, or storing a correction table with corrections for various path lengths or calculating the corrections with a predetermined empirical equation.

If desired, the servo system can be set to produce a null for a given value of absorbance for each wavelength to be scanned, and this will simplify the calculation required to determine the actual absorbance. For a null value of 1 Au or 1/10 of the reference and a path length of 1 cm, for example, the relationship for determining the absorbance becomes:

$$A(L) = (1Au)(D/1 \text{ cm}) \quad (4)$$

Referring now to FIGS. 5 through 8 of the drawings, they illustrate a preferred specific configuration for implementing the probe arrangement shown schematically in FIG. 4 of the drawings.

FIG. 5 is a top view, and FIG. 6 is a side view of the probe assembly. Referring first to FIG. 6 of the drawings, the reflector 49 appears at the left-hand end of the drawings and it is mounted in an assembly 52 which is supported by the two rods 54 which in turn are secured to the threaded plate 56, actuated by the threaded rod 58 which is in turn rotated by the handle 60 within the protective housing 62 at the opposite end of the entire assembly.

Incidentally, the fluid which is being measured spectrally is within a container or conduit generally indicated by the dashed lines 64. The probe assembly is provided with pipe threads 66 by which it is secured to the conduit or container 64. The single strand waveguides 68 and 70 are coupled at the left-hand end of the probe to the lenses 72 and 74, which couple the optical waveguides 68 and 70 to the window structures 76 and 78, respectively. The assembly 52 may be moved from the indicated position to that shown in dashed lines at 52', where the path length through the fluid being sampled has been reduced substantially to zero.

The probe structure which has been discussed up to this point is mounted in or to the tube 82, which has a cylindrical outer surface. In addition, the assembly 52 on which the reflector 49 is mounted, is of a slightly smaller diameter than the tube 82. The outer assembly 84 includes the mounting plate 86, the valve assembly 88, and an enclosing tubular housing 90 provided with a pair of seals 92 and 94 which engage the outer surface of the cylindrical tube 82 at two locations to prevent the escape of the fluid to be measured from the container or conduit 64. With the valve 88 in the open position as shown in FIG. 6, the probe including the tube 82 may be readily slid into position as indicated in this figure. In the event that there is liquid under some pressure within the chamber 64, the inner tube 82 may be inserted partially into the outer assembly 84, so that it is sealed at least at the seal 94, with the valve 84 being closed. Then, with the sample cell being forced from right to left as shown in FIGS. 5 and 6, the valve is opened, and the cell is pushed the remaining distance from right to left to the position shown in FIGS. 5 and 6. The seal 94 is then tightened up to hold the unit in position. Of course, when the valve 88 is closed, the inner tube 98 is rotated to a position 90 degrees displaced from that shown in FIG. 6, so that the channel is closed, and the vessel 64 is sealed.

When it is desired to shift the position of the reflector 49, the housing 62 is removed, and the handle 60 is rotated, thus turning the threaded shaft 58, and moving the threaded plate 56 in one direction or the other. Of course, this moves the rods 54 axially, carrying the housing 52 and the reflector 49 to the desired position.

The change in the gap length is, of course, twice the distance by which the unit 52 is moved. Half length calibration is accomplished by the plate 102 which has a threaded central opening which is engaged by the threads 104 on the shaft to which the handle 60 is secured. Mounted on the plate 102 are two calibrated arms 106 bearing vernier indicia so that the rotation of the handle 60, and the corresponding position of the reflector 49 may be accurately measured and determined.

Instead of the handle 60, and the rods 106 bearing indicia, the threaded shaft 104 may be rotated by a worm and gear arrangement in place of the handle, and with digital code wheel arrangements or other similar automatic read-out mechanisms being provided to indicate the position of the reflector. Various types of automatic shifting and sensing arrangements were mentioned hereinabove in connection with blocks 12 and 17 in FIG. 1 of the drawings.

The problem of light losses from causes other than absorption by the sample, such as formation of films or coatings on the windows to a cell, will now be considered. The formation of a coating on the cell window will be used as an example of losses of this type. If over a period of time a coating is formed on windows of the cell, a false reading may result because the coating itself is also absorbing. Some coatings absorb at substantially higher values than their thickness indicates because the coating condense on the windows, react with the windows, or are light sensitive and react with the light beam. To differentiate these losses which occur after the reference has been taken, a two path length probe approach has been developed. That is, by varying the probe path length over known distances any fixed serial addition of absorbance can be removed. Additional loss variations may be introduced with two separate path lengths, and a known reference without a sample is therefore taken to compensate for length dependent variations.

The following mathematical analysis shows how a filmed window need not prevent accurate determination of fluid absorbance.

$$A_1 = ecD_1 + A \quad (5)$$

$$A_2 = ecD_2 + A \quad (6)$$

$$A_T = A_1 - A_2 = ec(D_2 - D_1)K \quad (7)$$

Where:
$A_1$: Total absorbance at Length $D_1$
$A_2$: Total absorbance at Length $D_2$
e: molar absorbtivity
c: concentration
A: absorbance due to window coating or other cause not related to absorption of light by the sample
$A_T$: total absorbance less window absorbance
K: correction factor between the two path lengths.

Accordingly, the fact that the bulk absorbance varies linearly with path length, while film absorbance is constant, is employed to calculate the true absorbance of the fluid corresponding to the effective path length, $D_2 - D_1$.

It is apparent from the foregoing that a new and improved apparatus and method for measuring absorbance have been provided. While only certain presently preferred embodiments have been described in detail, as will be apparent to those familiar with the art, certain changes and modifications can be made. Thus, by way of example and not of limitation, other mechanical arrangements may be employed to shift the position of the reflector 52 in FIGS. 6 and 7; and the variable spacing sensing head 12 may have its spacing varied by a motor without using servo control to implement the film checking procedure, for example. Accordingly, the present invention is not limited to the arrangements as specifically shown and described hereinabove.

What is claimed is:

1. In an apparatus for determining the spectral absorbance of a sample;
   means for passing the light through the sample;
   means for varying the length of the path of the light passing through the sample to control the amount of light absorbed by the sample;
   means for determining the absorbance of the sample from the length of the path and the amount of light passing through the sample;
   said apparatus including an outer tube, means for securing said tube to a conduit or chamber containing fluid to be measured, an inner spectrophotometry cell including an optical channel having variable gap means for varying said sample path length, means including at least two seals for sealing said cell within said outer tube, and valve means for closing said outer tube while said cell is sealed within said outer tube by at least one of said seals, whereby said cell may be inserted into and removed from said conduit or chamber without significant loss or escape of the fluid being measured.

2. An apparatus as defined in claim 1 including graduated measuring means for determining the path length in the sample.

3. In a method of determining the spectral absorbance of a sample, the steps of: passing light through the sample; varying the length of the path of the light passing through the sample to control the amount of light absorbed by the sample; determining the absorbance of the sample from the length of the path and the amount of light passing through the sample; and
   performing the foregoing steps utilizing an apparatus having an outer tube including a valve and at least two seals for engaging an inner spectrophotometry assembly, and further including the steps of sealing the inner assembly within said outer tube, actuating said value, and then shifting the position of said spectrophotometry assembly within said outer tube, whereby said spectrophotometry assembly may be mounted to take samples or removed without significant loss or escape of the fluid being measured.

4. A method as defined in claim 3 wherein said method includes the step of making each measurement with two different path lengths; and
   calculating the absorbance of the sample fluid sample, from said two measurements, despite the presence of a film on optical surfaces included in the light path through the sample.

5. A method as defined in claim 4 wherein said calculating step is accomplished in accordance with the following expressions:

$$A_1 = ecD_1 + A$$

$$A_2 = ecD_2 + A$$

$$A_T = A_1 - A_2 = ec(D_2 - D_1)K$$

Where:
$A_1$: Total absorbance at Length $D_1$
$A_2$: Total absorbance at Length $D_2$
e: molar absorbtivity
c: concentration
A: absorbance due to window coating or other cause not related to absorption of light by the sample
$A_T$: total absorbance less window absorbance
K: correction factor between the two path lengths.

6. In an apparatus for determining the spectral absorbance of a sample:

a light source;

single strand optical waveguide means for directing light from said light source through the sample;

light intensity measuring means;

optical waveguide means for coupling light which has passed through said sample to said light intensity measuring means;

means for varying the length of the path of the light passing through the sample to control the amount of light absorbed by the sample without changing the length of the optical path from said light source to said sample and from said sample to said measuring means;

means for determining the length of the path and the corresponding intensity as measured by said measuring means, whereby the sample absorbance may be calculated;

said means for passing light through the sample and coupling light to said measuring means including a pair of optical waveguides having end portions separated by a gap and aligned for transmitting and receiving light through the sample, and the means for varying the length of the path including means for moving one of the waveguides to adjust the width of the gap; and said apparatus including means defining a chamber for the sample, a pair of probes connected to the waveguides and positioned in axial alignment within the chamber on opposite sides thereof, fluid inlet and outlet means for delivering the sample to and from the chamber, and means for moving one of the probes to vary the spacing between the probes.

7. The apparatus of claim 6 including a lens carried by each of the probes for collimating the light

* * * * *